US00PP19909P3

(12) United States Plant Patent
Richard

(10) Patent No.: US PP19,909 P3
(45) Date of Patent: Apr. 14, 2009

(54) APPLE TREE NAMED 'GALAVAL'

(50) Latin Name: *Malus domestica Borkh*
Varietal Denomination: Galaval

(75) Inventor: Albert Richard, Corze (FR)

(73) Assignee: Pepinieres du Valois SARL, Villers-Cotterêts (FR)

( * ) Notice: Subject to any disclaimer, the term of this patent is extended or adjusted under 35 U.S.C. 154(b) by 0 days.

(21) Appl. No.: 11/986,605

(22) Filed: Nov. 20, 2007

(65) Prior Publication Data

US 2008/0141402 P1 Jun. 12, 2008

(51) Int. Cl.
*A01H 5/00* (2006.01)

(52) U.S. Cl. ..... Plt./161

(58) Field of Classification Search ..... Plt./161
See application file for complete search history.

*Primary Examiner*—Annette H Para
*Assistant Examiner*—S. B. McCormick Ewoldt
(74) *Attorney, Agent, or Firm*—Stratton Ballew PLLC

(57) ABSTRACT

A new apple tree named 'Galaval' is described. 'Galaval' is a mutation of 'Galaxy' selected for its interesting over color intensity. Fruit of 'Galaval' is distinguished from fruit of 'Galaxy' and other Gala-type varieties by its intense dark purple-brown skin over color with no defined stripes.

8 Drawing Sheets

Latin name: *Malus domestica* Borkh.
Variety denomination: 'Galaval'.

BACKGROUND OF THE VARIETY:

'Galaval' is a new and distinct cultivar of apple tree *Malus domestica* Borkh. This new cultivar is a product of a whole tree mutation of 'Galaxy' (U.S. Plant No. 6,955), and is characterized by fruit having an intense dark purple-brown over color with no defined stripes. 'Galaval' was first observed in an orchard situated at Corze (Loire Valley, France) in 2002. This variety was then asexually reproduced by budding and fruited through two successive generations in too different locations in France, Seiches sur Le Loir and Villers-Cotterêts. 'Galaval' has been observed to remain true to type over successive asexually propagated generations. The color, presentation and other characteristics of this variety also remained the same through two generations.

BRIEF DESCRIPTION OF THE VARIETY

'Galaval' was first selected for its interesting over color intensity. It is distinguished from other known Gala-type varieties by its intense dark purple-brown over color fruit skin with no defined stripes. 'Galaval' is also well characterized by a globose to flat shape. The distinctive characteristics are shown in Table 1 below.

TABLE 1

Comparison of 'Galaval' to other known Gala strains.

| Variety | Skin color | Percentage of Overcolor | Pattern of Overcolor |
|---|---|---|---|
| Galaval | Dark purple brown (RHS 59A) | 95-100% (avg.: 98.25%) | No defined stripes |
| Simmons | Dark red (RHS 45A) | 80-100% (avg.: 90.5%) | Weakly defined stripes |
| Galaxy | Red (RHS 47A) | 50-90% (avg.: 74%) | Well defined stripes |

BRIEF DESCRIPTION OF THE PHOTOGRAPHS

FIG. 1 illustrates the difference in fruit skin color between 'Galaval', 'Simmons Gala' (U.S. Plant Pat. No. 10,840) and 'Galaxy' at picking lime.

DETAILED BOTANICAL DESCRIPTION OF THE VARIETY

Figure 1:
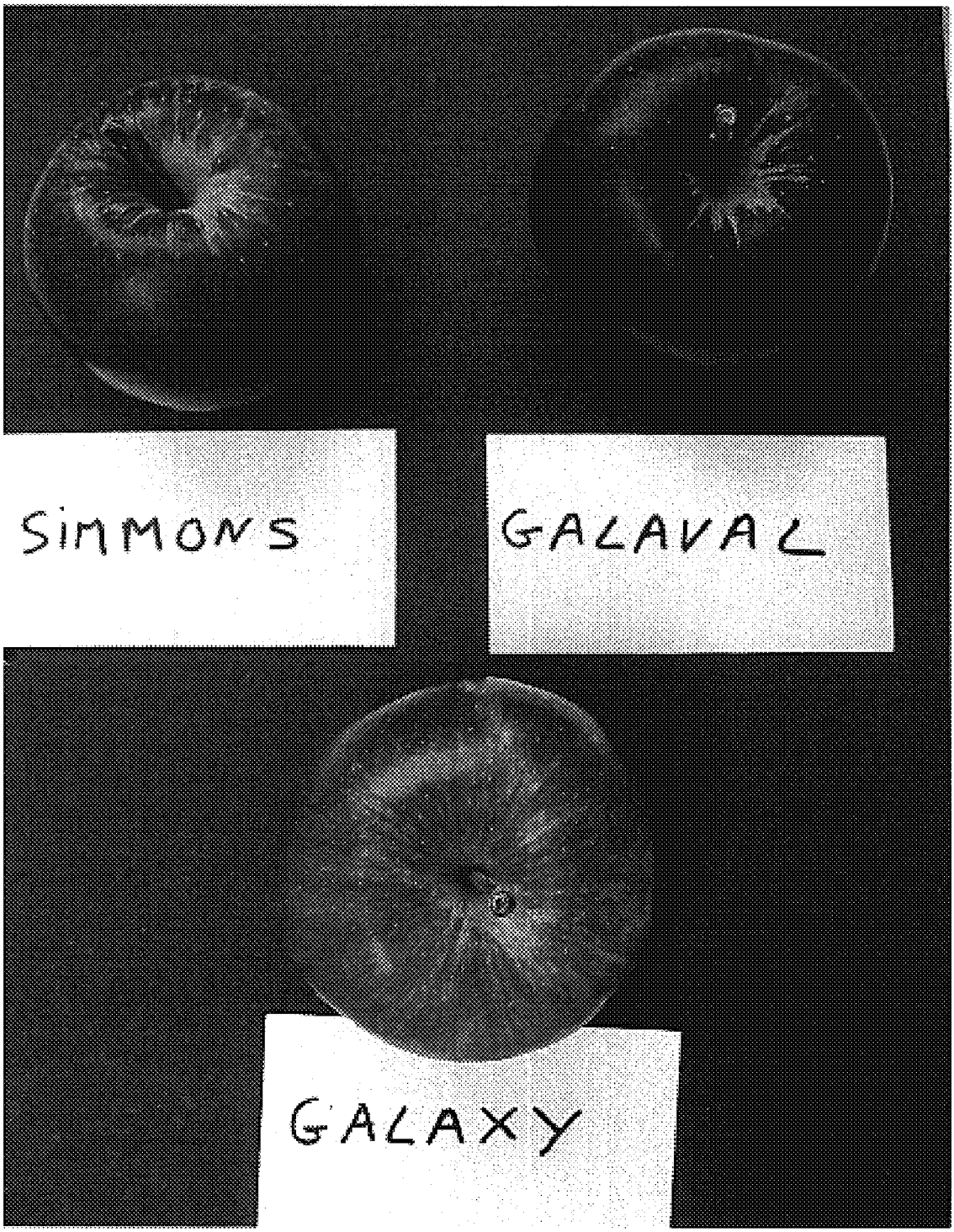
Figure 2:
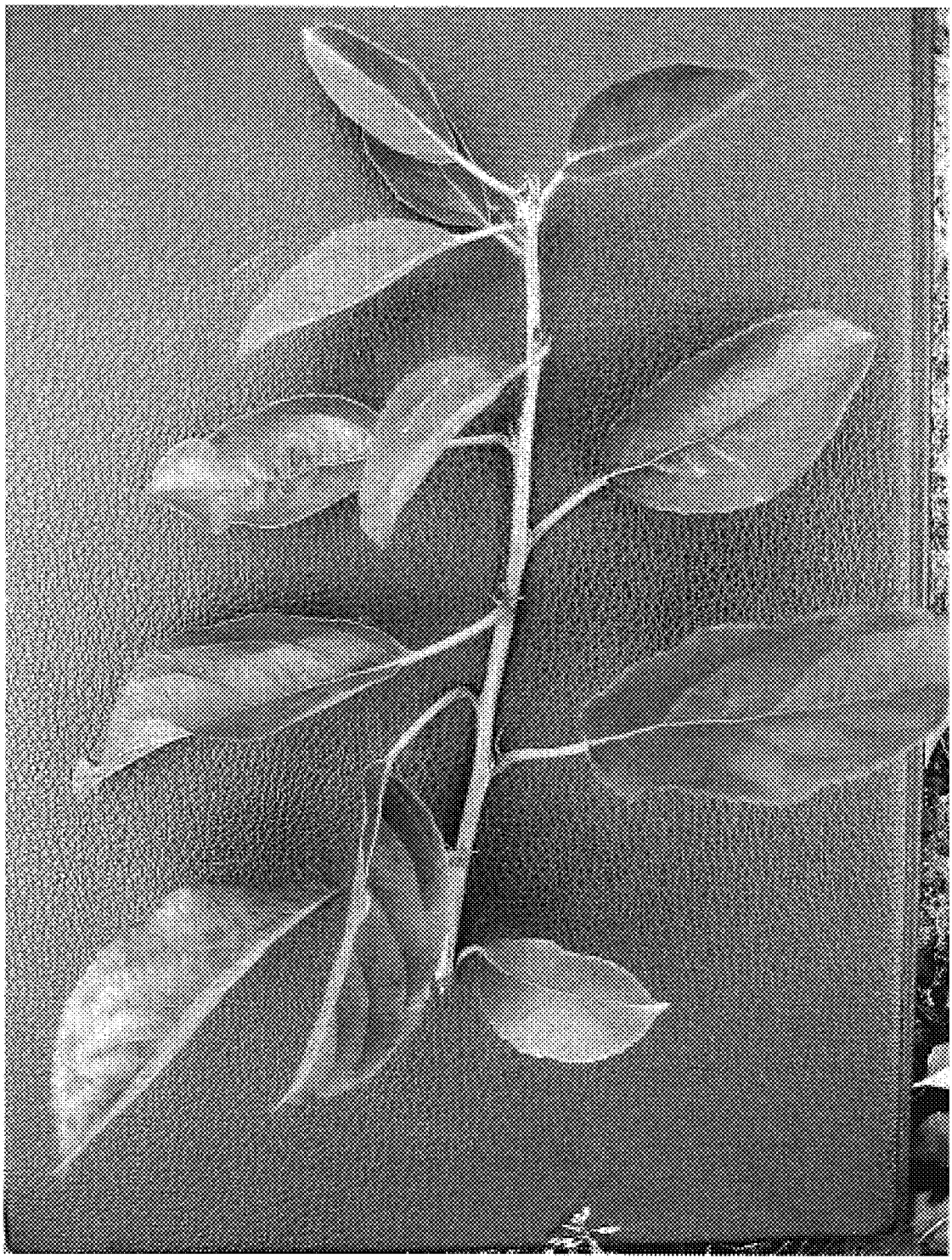
FIG. 2 shows a one-year old bore shoot of 'Galaval' 30 days after picking time.
Figure 3:
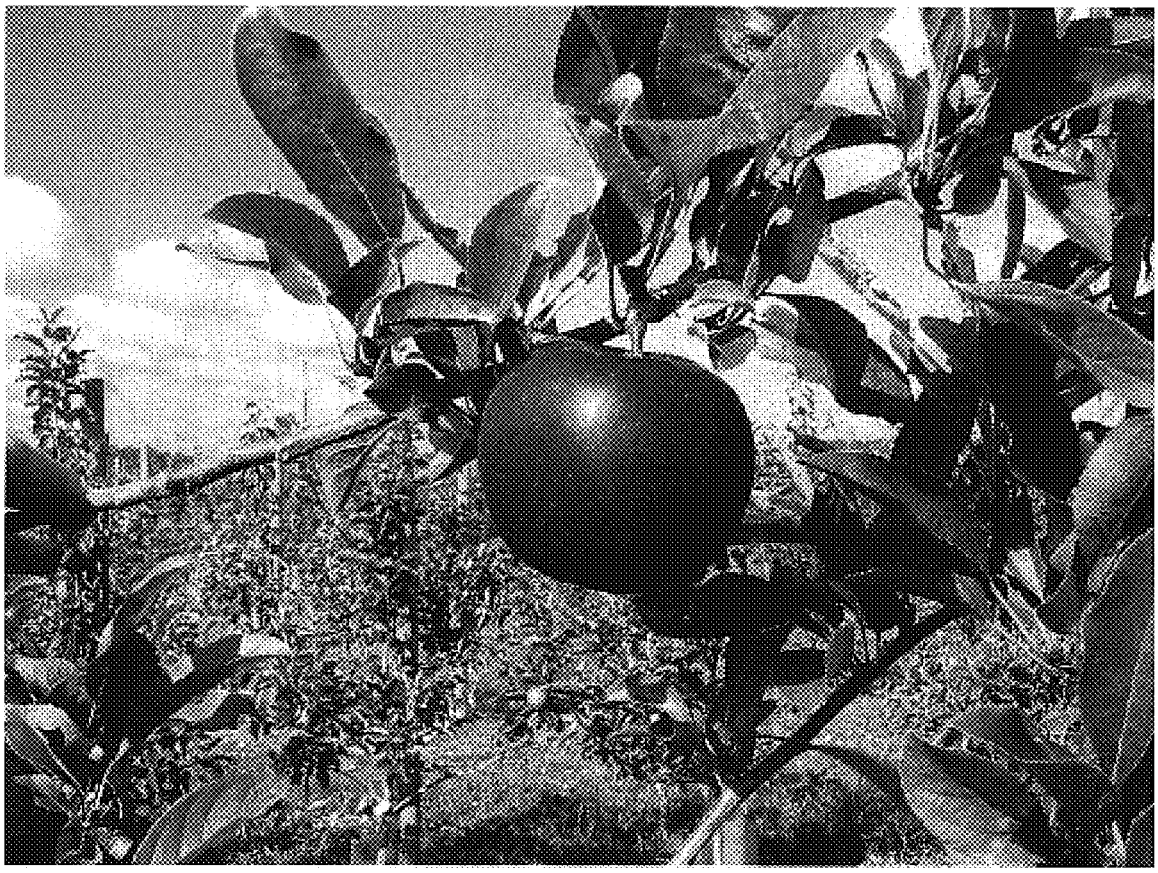
FIG. 3 shows fruit of 'Galaval' 7 days before picking time.
Figure 4:
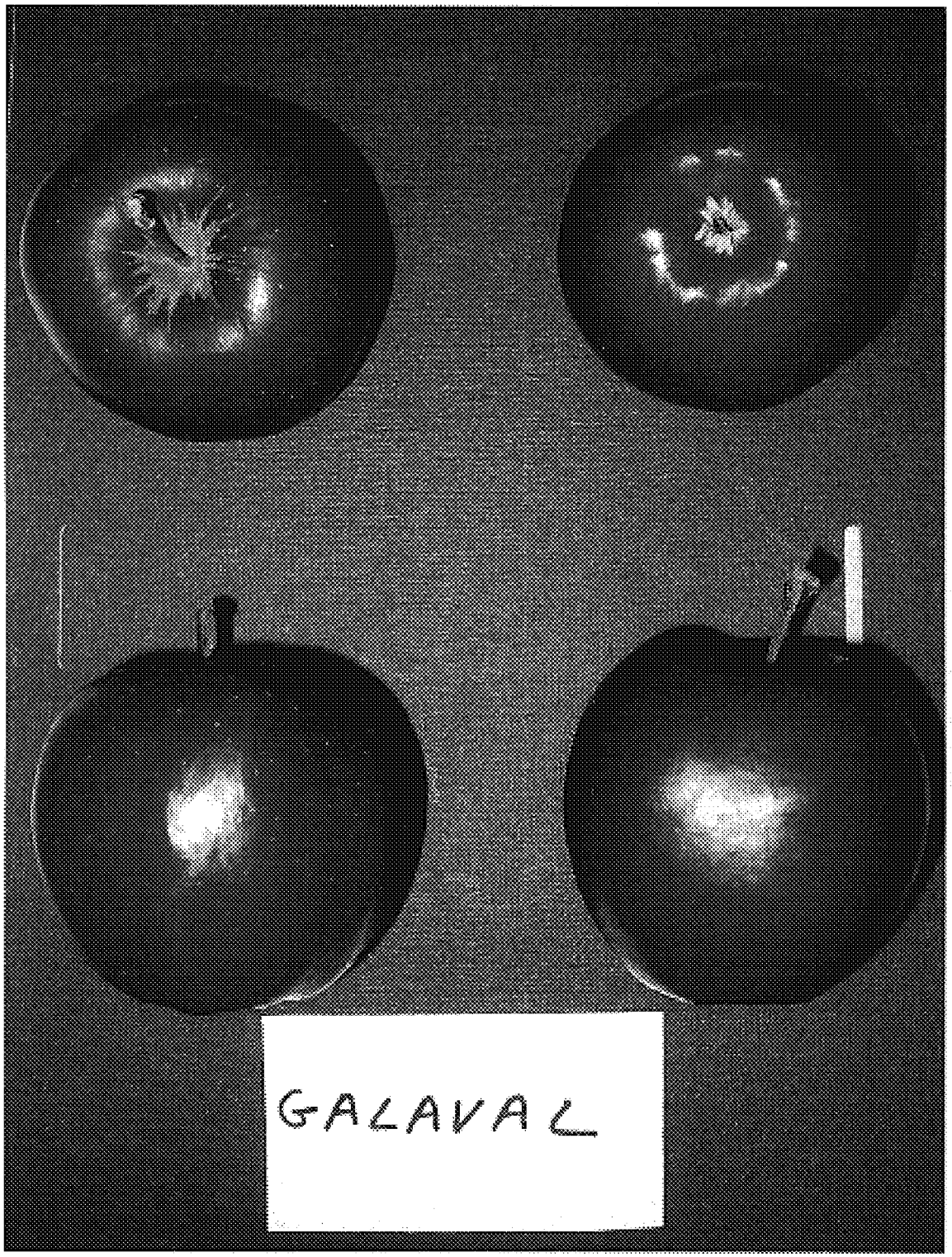
FIG. 4 shows fruit of 'Galaval' after 30 days of storage.
Figure 5:
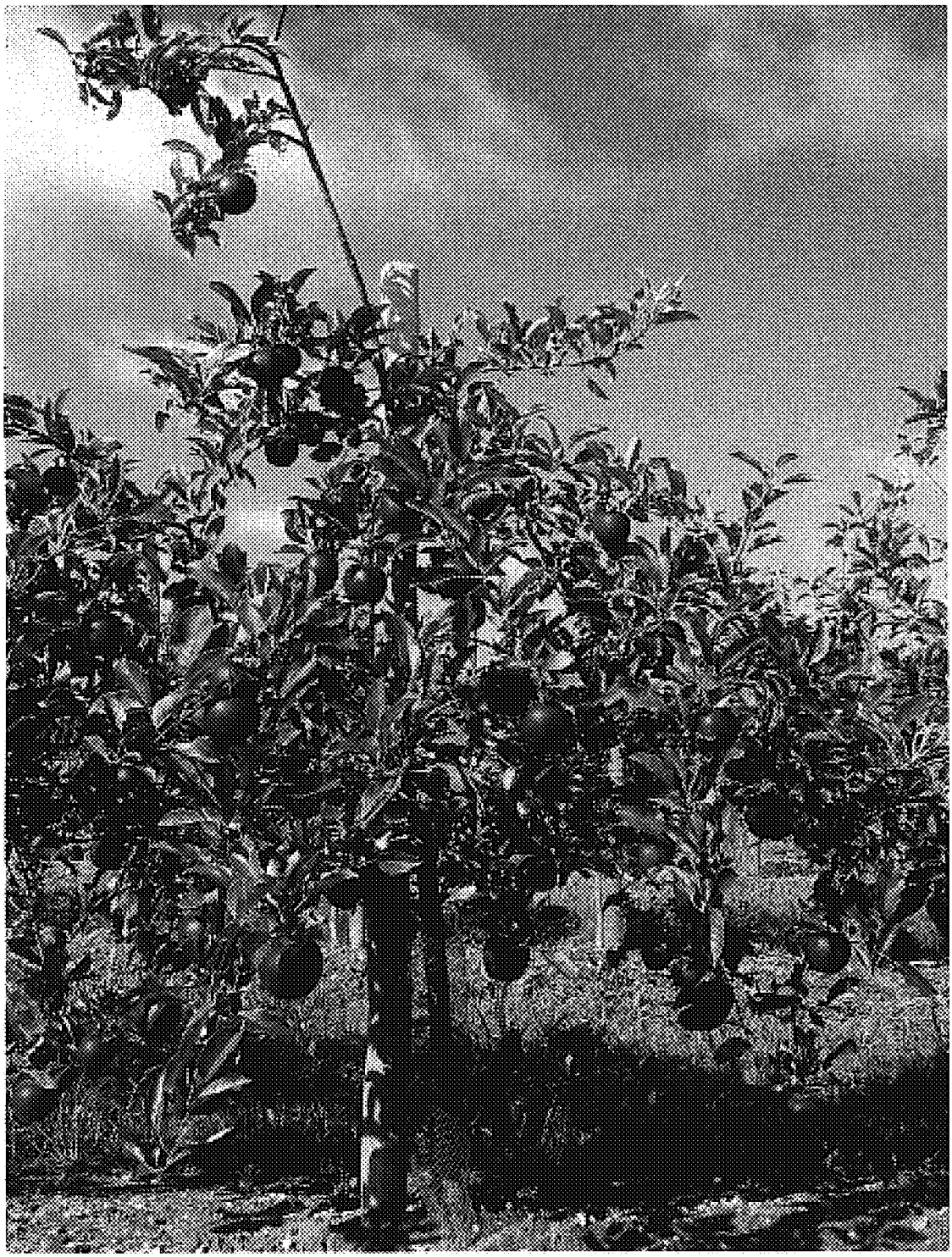
FIG. 5 shows a two year old 'Galaval' second generation tree with fruit at picking time.
Figure 6:
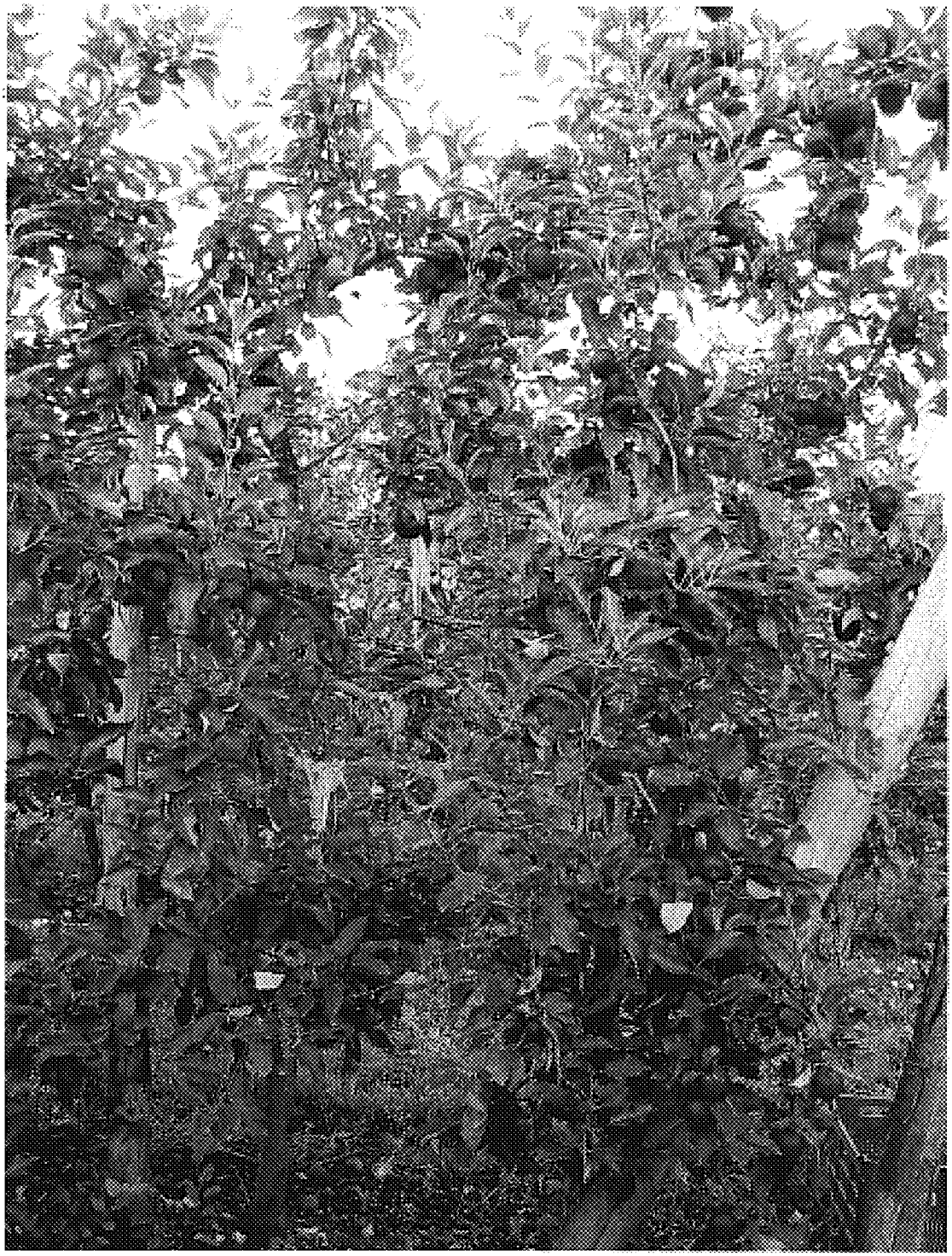
FIG. 6 shows the 'Galaval' mother tree in the 'Galaxy' orchard at Corze.
Figure 7:
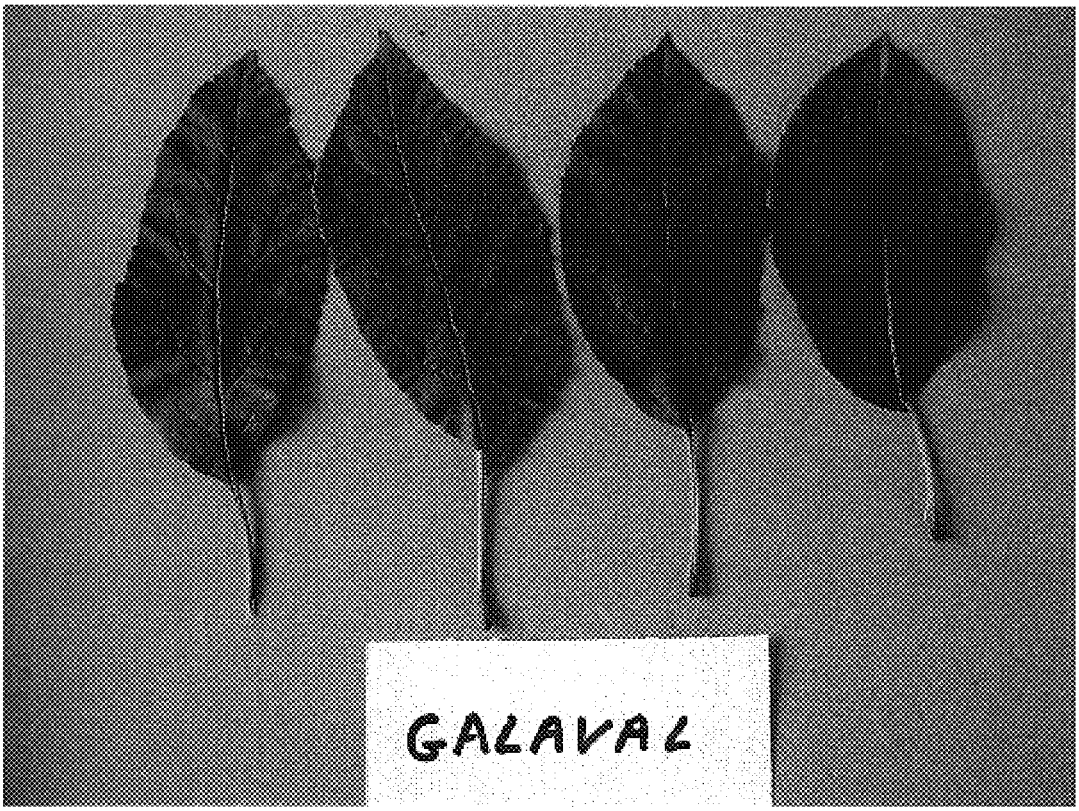
FIG. 7 shows representative leaves of 'Galaval'.
Figure 8:
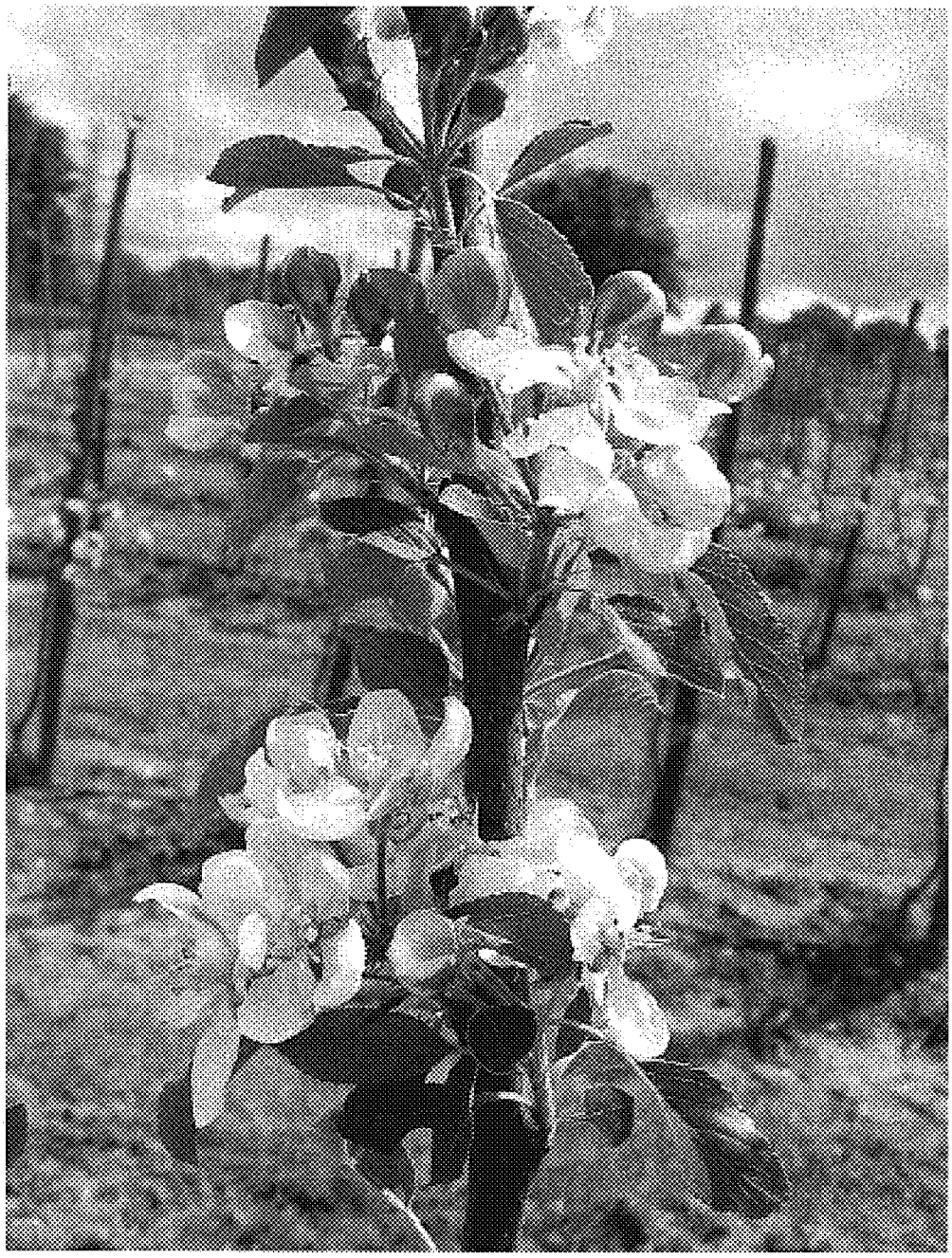
FIG. 8 shows flowers of 'Galaval' at full blossom.

The following-detailed botanical description is based on observations made during the 2007 growing season at Seiches sur le Loir, France of two year old trees grown on 'M9' rootstock (not patented) in high density plantings. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree: Vigor — medium (similar to 'Gala' strains); Type — ramified; Habit — spreading; Height — 2.20 m; Trunk diameter (at 30 cm above the graft) — medium (avg. 39 mm), Bark texture — smooth, similar to 'Simmons Gala'; Bark coloration — grey N200C.

Branch (fruiting branches located at around 1 m above the graft union): Length — long (avg. 1.17 m); Diameter — large (avg. 19 mm); Crotch angle 70° to 90°; Bark color — grey N200C.

One year old shoot: Length — short to medium (avg. 20 cm); Color — brown N199C; Pubescence (on upper half of the shoot) — medium ; Thickness — thin (avg. 3.5 mm); Internode length — medium (avg. 18 mm); Pubescence — medium (similar to 'Gala' strains); Number of lenticels — medium (7 lenticels per $cm^2$).

Flower buds: Quantity per spur — 1 to 3; Shape — round to conical; Length — small to medium (avg. 11 mm); Diameter — small to medium (avg. 12 mm); Color — red purple N57A.

Flowers: Flower — medium size; Diameter of fully open flower — small to medium (avg. 29 mm); Relative position of petal margin — overlapping; Number per cluster — 5 to 6; Date of first bloom — April 15 in Loire Valley, France; Date of full bloom — April 20 in Loire Valley, France; Pollination requirement — 'Braeburn', 'Granny Smith', or other variety blooming at the same time.

Petals: Number per flower — 5; Shape — ovoid; Length — medium (avg. 17 mm); Widths — Medium (avg. 13 mm); Apex — round; Base — conical-pointed; Margin — smooth; Coloration of upper surface — white N155C; Coloration of lower surface — white N155B.

Pistils: Size — Medium (avg. 13 mm); Color-yellow green N144C.

Stigma: Size — small to medium (avg. 0.6 mm); Color — yellow green 150B.

Style: Size — long (avg. 11 mm); Color — yellow green 145A.

Ovary: Size — medium (avg. 2 mm); Color — green 140A.

Anthers: Quantity — numerous (avg. 13 per flower); Size — medium (avg. 2.1 mm), Presence of pollen — present; Color of pollen — yellow 3C.

Pedicel: Size — medium to long (avg. 22 mm); Diameter — quite thin (avg. 1.4 mm); Color — green 143B.

Sepals: Quantity — 5; Coloration — green 143C; Shape — conical pointed.

Leaves: Shape — elliptic; Length (petiole not included) — medium-long (avg. 88 mm); Width — narrow (avg. 43 mm); Length/width ratio — medium to large (2.05); Blade margin — serrate; Apex — acuminate; Base shape — oblique; Color of upper surface — dark green 137A (in late summer); Color of lower surface — green 137C (in late summer); Attitude in relation to shoot — outward to downwards.

Petiole: Length — long (avg. 35 mm); Diameter — medium (avg. 1.5 mm); Coloration — green 137C.

Fruit: Quantity per cluster — (2 to 4); Diameter — small to medium (avg. 71 mm); Weight — medium (avg. 190 g); Ratio of height to width — medium (1.09); General shape in profile — globose to flat; Position of maximum diameter — in middle; Ribbing — weak; Crowning at calyx end — moderate; Size of eye — medium to large (avg. 16 mm); Aperture of eye — partially open; Length of sepal — medium (avg. 4 mm); Bloom of skin — weak; Greasiness of skin — weak; Background color of skin — light yellow 8C; Amount of over color — high; Over color of skin — Dark purple brown 59A: Intensity of over color — dark; Pattern of over color — solid flush with no defined stripes; Amount of russet around stalk cavity — medium; Amount of russet on cheeks — absent; Area of russet around eye basin — absent or very weak; Length of stalk — long (avg. 28 mm); Thickness of stalk — medium (avg. 1.9 mm); Depth of stalk cavity — medium (avg. 15.5 mm); Width of stalk cavity — narrow (avg. 12 mm); Depth of eye basin — medium (avg. 9.4 mm); Width of eye basin — medium (avg. 20 mm); Firmness of flesh — medium to firm; Flesh texture — medium to fine; Aroma — moderately aromatic and slightly sweet; Juiciness — medium to high; Brix — 11° Brix minimum at harvest time; Flesh coloration — light yellow 4D; Stem coloration — dark purple red 53A.

Seeds: Quantity per fruit — 5 on average; Shape — truncate ovoid; Coloration — dark brown 165A.

Harvest: Time for harvest — early, last week of August (similar to 'Galaxy'); Number of picks — one to two picks; Amount of fruit produced per tree per harvest — 60 fruits on third leaf trees.

Disease resistance/susceptibility: None noted.

Market use: Fresh.

I claim:

1. A new and distinct apple tree substantially as described and illustrated herein.

* * * * *